United States Patent
Parthun et al.

(10) Patent No.: US 12,023,234 B2
(45) Date of Patent: *Jul. 2, 2024

(54) METHOD AND SYSTEM FOR ASEPTICALLY FILLING A PACKAGE

(71) Applicant: Medline Industries, LP, Northfield, IL (US)

(72) Inventors: William Parthun, Highland Park, IL (US); Edward Danavi, Palatine, IL (US)

(73) Assignee: Medline Industries, LP, Northfield, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/984,173

(22) Filed: Nov. 9, 2022

(65) Prior Publication Data

US 2023/0062914 A1 Mar. 2, 2023

Related U.S. Application Data

(60) Continuation of application No. 17/197,934, filed on Mar. 10, 2021, now Pat. No. 11,523,947, which is a
(Continued)

(51) Int. Cl.
*A61F 15/00* (2006.01)
*A61L 2/08* (2006.01)
(Continued)

(52) U.S. Cl.
CPC ............ *A61F 15/001* (2013.01); *A61L 2/087* (2013.01); *B65B 3/003* (2013.01); *B65B 5/045* (2013.01);
(Continued)

(58) Field of Classification Search
CPC ....... B65B 5/045; B65B 55/16; B65B 55/027; B65B 3/003; B65B 43/465; B65B 43/52;
(Continued)

(56) References Cited

U.S. PATENT DOCUMENTS

| | | |
|---|---|---|
| 3,017,990 A | 1/1962 | Sol |
| 4,581,874 A | 4/1986 | Rechtsteiner et al. |

(Continued)

FOREIGN PATENT DOCUMENTS

| | | |
|---|---|---|
| KR | 20040023449 A | 3/2004 |
| KR | 20040047090 A | 6/2004 |
| WO | 2014035981 A1 | 3/2014 |

OTHER PUBLICATIONS

Proceedings Before the Food and Drug Administration Center for Drug Evaluation and Research Advisory Committee for Pharmaceutical Science and Clinical Pharmacology (Aug. 5, 2009). Web. Sep. 27, 2013. <http://www.fda.gov/downloads/AdvisoryCommittees/CommitteesMeetingMaterials/Drugs/AdvisoryCommitteeforPharmaceuticalScienceandClinicalPharmacology/UCM179891.pdf>.

(Continued)

*Primary Examiner* — Thomas M Wittenschlaeger
(74) *Attorney, Agent, or Firm* — Gurr Brande & Spendlove, PLLC; Robert D. Spendlove (57) ABSTRACT

The present invention relates to a method and system for aseptically filling of flexible packages containing dry cloth. Such a method may include a first stage that is performed in a non-sterile environment. The first stage may include cutting a first substantially dry cloth to a predetermined size; inserting the first cloth into a flexible package; sealing a first end of the flexible package; and sterilizing the flexible package. The method may also include a second stage performed in a sterile environment. The second stage may include filling the flexible package with a medical solution such that the substantially dry cloth absorbs at least a portion of the medical solution; and sealing the open end of the flexible package.

20 Claims, 7 Drawing Sheets

Related U.S. Application Data continuation of application No. 16/287,867, filed on Feb. 27, 2019, now Pat. No. 10,945,895, which is a division of application No. 13/759,759, filed on Feb. 5, 2013, now Pat. No. 10,219,957.

(51) Int. Cl.
| | | |
|---|---|---|
| *B65B 3/00* | (2006.01) | |
| *B65B 5/04* | (2006.01) | |
| *B65B 55/02* | (2006.01) | |
| *B65B 55/16* | (2006.01) | |
| *B65B 43/46* | (2006.01) | |
| *B65B 43/52* | (2006.01) | |
| *B65B 51/14* | (2006.01) | |

(52) U.S. Cl.
CPC ............ *B65B 55/027* (2013.01); *B65B 55/16* (2013.01); *A61L 2202/181* (2013.01); *B65B 43/465* (2013.01); *B65B 43/52* (2013.01); *B65B 51/146* (2013.01)

(58) Field of Classification Search
CPC ...... B65B 51/146; A61F 15/001; A61L 2/087; A61L 2202/181
See application file for complete search history.

(56) References Cited

U.S. PATENT DOCUMENTS

| | | | |
|---|---|---|---|
| 4,726,170 A | | 2/1988 | Sawa et al. |
| 4,749,080 A | | 6/1988 | Toohey |
| 4,896,768 A | | 1/1990 | Anderson |
| 5,014,494 A | | 5/1991 | George |
| 5,688,476 A | * | 11/1997 | Bourne .................... B32B 7/05 206/439 |
| 5,690,968 A | | 11/1997 | Ross et al. |
| 5,730,934 A | | 3/1998 | Holbert |
| 5,753,246 A | | 5/1998 | Peters |
| 5,879,620 A | | 3/1999 | Cohen |
| 5,879,693 A | | 3/1999 | Wolfe |
| 6,096,358 A | | 8/2000 | Murdick et al. |
| 6,328,811 B1 | | 12/2001 | Martin et al. |
| 7,066,916 B2 | | 6/2006 | Keaty, Jr. et al. |
| 7,427,574 B2 | | 9/2008 | Allen |
| 7,595,021 B2 | | 9/2009 | Keaty, Jr. et al. |
| 7,935,093 B2 | | 5/2011 | Hanifl et al. |
| 8,221,365 B2 | | 7/2012 | Keaty, Jr. et al. |
| 8,337,752 B2 | | 12/2012 | Yamamoto et al. |
| 8,375,686 B2 | | 2/2013 | Caudle et al. |
| 10,945,895 B2 | * | 3/2021 | Parthun .................. B65B 55/16 |
| 2003/0226857 A1 | | 12/2003 | Bibbo et al. |
| 2007/0042666 A1 | | 2/2007 | Allen |
| 2007/0119121 A1 | | 5/2007 | Woods et al. |
| 2007/0293441 A1 | | 6/2007 | Choo et al. |
| 2009/0173039 A1 | | 7/2009 | Slomski et al. |
| 2010/0227926 A1 | | 9/2010 | Keaty, Jr. et al. |
| 2010/0296967 A1 | * | 11/2010 | Yamamoto ................ A23L 3/04 422/26 |
| 2011/0129520 A1 | | 6/2011 | Bogdansky et al. |
| 2011/0146204 A1 | | 6/2011 | Caudle et al. |
| 2012/0222774 A1 | | 9/2012 | Husnu et al. |
| 2021/0220192 A1 | | 7/2021 | Parthun et al. |

OTHER PUBLICATIONS

Food and Drug Administration Center for Drug Evaluation and Research, Department of Health and Human Services, Public Hearing, Antiseptic Patient Preoperative Skin Preparation Products, Dkt. No. FDA-2012-N-1040 (Dec. 12, 2012). Web. Sep. 27, 2013. <http://www.fda.gov/downloads/drugs/newsevents/ucm334694.pdf>.

Notification of Transmittal of the International Search Report and the Written Opinion of the International Searching Authority, or the Declaration; International Application No. PCT/US2014/014616, Medline Industries, Inc. (Parthun, William, et al.); dated May 20, 2014.

* cited by examiner

METHOD AND SYSTEM FOR ASEPTICALLY FILLING A PACKAGE

RELATED APPLICATION

This application is a continuation of U.S. patent application Ser. No. 17/197,934 filed on Mar. 10, 2021 entitled "METHOD AND SYSTEM FOR ASEPTICALLY FILLING A PACKAGE," which is a continuation application of U.S. patent application Ser. No. 16/287,867 filed Feb. 27, 2019 and issued as U.S. Pat. No. 10,945,895 on Mar. 16, 2021, entitled "METHOD AND SYSTEM FOR ASEPTICALLY FILLING A PACKAGE," which is a divisional of U.S. patent application Ser. No. 13/759,759 filed Feb. 5, 2013 and issued as U.S. Pat. No. 10,219,957 on Mar. 5, 2019, entitled "METHOD AND SYSTEM FOR ASEPTICALLY FILLING A PACKAGE," the contents of each of which are herein incorporated by reference in their entirety.

BACKGROUND

Some embodiments relate generally to aseptically filling a package and more particularly to aseptically filling a package containing a cloth with a medical solution for use in healthcare.

The healthcare and other industries use aseptic and/or sterile products, for example, cloths to clean wounds and prepare a patient for surgery. Such cloths can be at least partially saturated with a medical solution, for example, an alcohol solution. Another medical solution that may be used is Chlorhexidine gluconate ("CHG").

CHG is a chemical antiseptic that is currently approved and marketed for both inpatient and outpatient use in skin cleansing products, oral rinses, and in pre-surgical applications. Chlorhexidine gluconate is a potent membrane-active anti-bacterial agent with activity against a broad range of Gram-positive and Gram-negative bacteria. At low concentrations, CHG is bacteriostatic, disrupting cell membrane function. At higher concentrations, CHG is bactericidal against a wide range of bacteria and yeast, irreversibly disrupting cell membrane integrity and leading to intracellular leakage.

The chemical name of CHG is 2,4,11,13-Tetraazatetradecanedimidamide, N,N"-bis(4-chlorophenyl)-3,12-diimino-, di-D-gluconate. The empirical formula of CHG is $C_{22}H_{30}Cl_2N_{10} \cdot 2C_6H_{12}O_7$ and its molecular weight is 897.76.

Chlorhexidine gluconate was first approved by the Topical Antimicrobials Committee of the FDA in 1976 as a surgical hand scrub under the tradename Hibiclens®. Since then, multiple other CHG products have also been approved by the FDA for various antiseptic indications. In hospitals, CHG is commonly used for surgical site preparation and as a skin cleanser to reduce the number of microorganisms on the skin.

Current methods of sterilizing healthcare products, however, are either unsuitable for the contents of a package using CHG or other medical solutions, or they may degrade one or more qualities of the medical solution.

Thus, there is a need for a method of aseptically filling a package for medical use.

DETAILED DESCRIPTION

In describing the embodiments of the invention in detail and referring to the drawings, like numbers indicate like parts throughout the figures. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions.

As used in this specification the term sterile can mean a sterile environment, process and/or product in that is free from contaminants in accordance with a government and/or organizational regulation to a first level of assurance. In some embodiments, the first level of assurance can be 10-6. Similarly, the term aseptic can mean a sterile environment, process and/or product in that is free from contaminants in accordance with a government and/or organizational regulation to a second level of assurance, less stringent than the first level of assurance. In some embodiments, the first level of assurance can be 10-3. As used in this specification, the term sterile can include both sterile and aseptic unless specifically noted.

Figure 1:
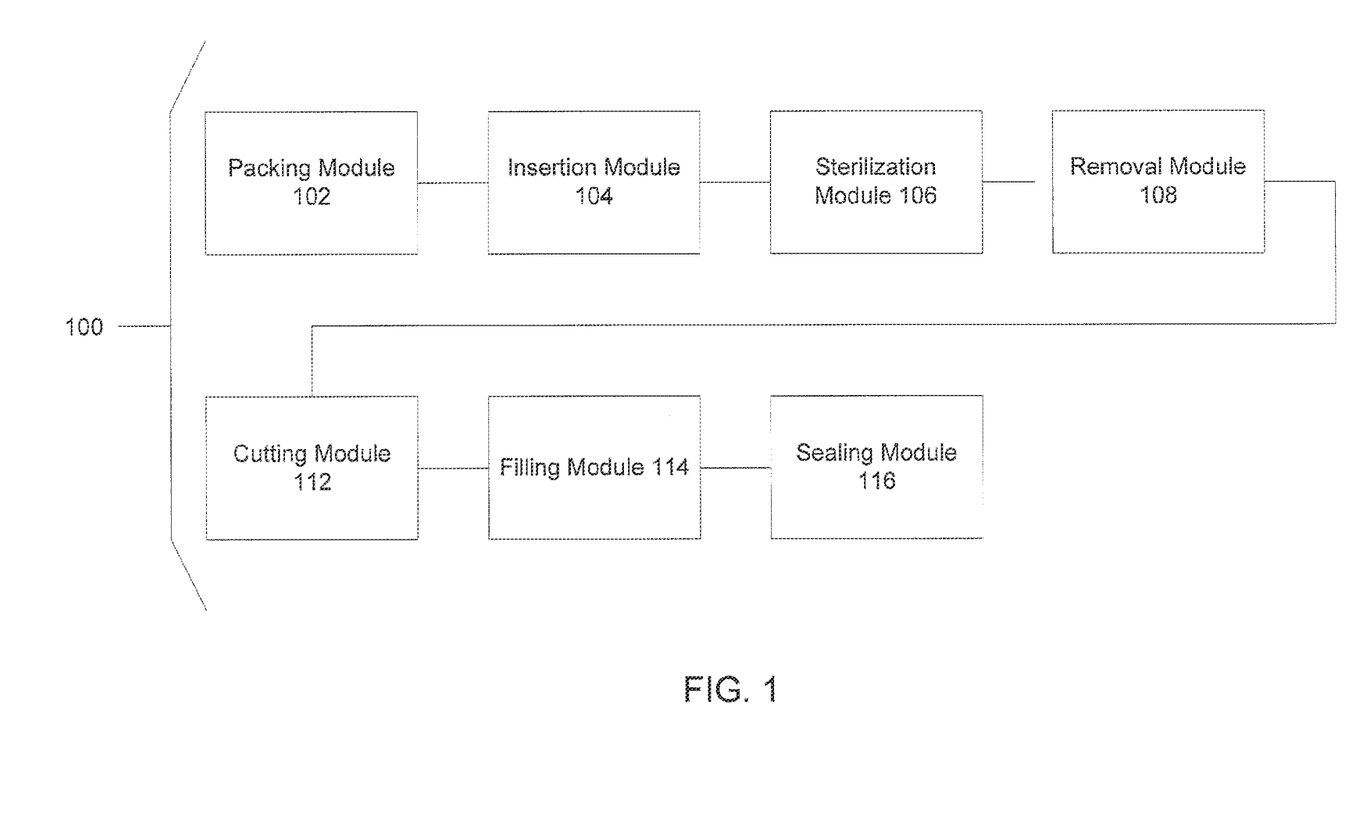
FIG. 1 is a schematic illustration of a system for filling a package according to an embodiment.

As shown schematically in FIG. 1, a system 100 can be used to prepare a package containing a cloth and a medical solution for shipping. Specifically, system 100 can be used to dispose a dry cloth into the package, sterilize the package containing the cloth, aseptically fill the package with a medical solution, and seal the package for further packing and/or shipping. The system 100 can include various modules for performing associated steps of a packaging process. For example, system 100 may include a packing module 102, an insertion module 104, a sterilization module 106, a removal module 108, a cutting module 112, a filling module 114 and a sealing module 116. In some embodiments, system 100 can include a mechanized component to move a package from one module to another module for example, a conveyor module (not shown).

In some embodiments, each of the components of system 100 can be disposed in a room, such as, for example, a clean room in accordance with a clean room classification, such as, for example, an ISO clean room standard. In some embodiments, the components of system 100 can be distributed over more than one room. In such embodiments, a first room can be in a first location, and a second room can be in a second location, different from the first location, and the first location and second location can be separated by an intermediate location that may not be in accordance with a clean room standard and/or may be a different clean room standard than the first room and/or the second room. In further embodiments, some steps of a process performed by system 100 may be conducted in a non-sterile environment, while other steps are conducted in sterile environments with varying levels of sterility assurance in order to achieve a finished product, including a packaged cloth with medical solution, having a certain level of sterility. In one embodiment, the finished product has been rendered sterile to a sterility assurance of at least $10_{-3}$. In a further embodiment, the finished product has been rendered sterile to a sterility assurance of at least $10_{-6}$. In another embodiment, a first portion of the finished product can have been rendered sterile to a first sterility assurance, for example, at least 10-3, and a second portion can have been rendered sterile to a second sterility assurance, for example, at least 10-6.

Figure 3:
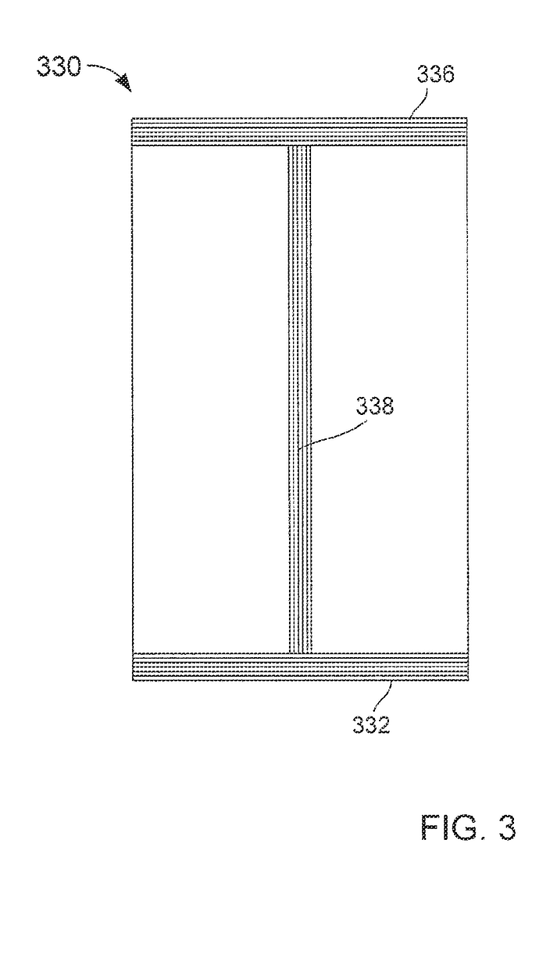
FIG. 3 is an illustration of a package according to a second embodiment.

As described above, system 100 can be used to pack and/or fill packages. In an embodiment, the package may be a flexible package as illustrated in FIG. 3. Such a package may be constructed from a flexible film. For example, the package material may be 0.48 mil PET/0.48 mil PET/2.25 mil HDPE COEX film. In some embodiments, the package may be constructed of a different flexible film and/or can have different level of flexibility. In such an embodiment, the package can be substantially rigid, for example, a plastic tub. The package is constructed by folding a sheet of film into a generally tubular configuration and sealing the two abutting ends of the film together along seam 338. The package may then be sealed by applying appropriate sealing temperatures and parameters to create sealed ends 332 and 336. The step of sealing the ends 332,336 may occur at different stages of the process as described below.

Returning to FIG. 1, packing module 102 can insert a cloth into the package. In some embodiment packing module 102 can be configured to receive the cloth having been previously cut to size and shape. In other embodiments, packing module 102 can include a cutting component (not shown) that can be configured to receive cloth, for example, a bundle or roll of cloth, and can be configured to cut the cloth to a predetermined size and/or shape prior to packing the cloth in the package. In some embodiments, the cloth can be folded prior to packing in the package. In some embodiments, packing module 102 can pack a plurality of cloths into the package. In such embodiments, the plurality of cloths can be stacked, folded, or the like.

In an embodiment, each package will include two 8 inch by 8 inch cloths. Suitable cloths may include polyester, rayon, other natural and/or artificial fibers and/or blends. Additionally, suitable cloths can include different size fibers. In some embodiments, a cloth can be any shape and/or size. In some embodiments, a cloth can be similar to the cloths described in U.S. Pat. No. 7,427,574 entitled "Non-Woven Wash Cloth," U.S. Pat. No. 7,066,916 entitled "Disinfectant Delivery System, and Method of Providing Alcohol-Free Disinfection," and/or U.S. Pat. No. 7,595,021 entitled "Method of Providing Alcohol-Free Disinfection," each of which is herein incorporated by reference in their entirety.

Manufacturing of cloth related products includes a variety of challenges to maintaining a clean room environment. For example, slitting/cutting of the cloth material creates dust and loose fibers that increase the difficulty in maintaining the sterility of a manufacturing environment. In addition, there may be difficulties with effectively sterilizing large and/or dense rolls of cloth material. Accordingly, in embodiments of the present invention, steps of the process performed in the packaging module, including preparing the cloths and inserting them into the package, may be performed in a non-sterile environment.

Figure 2:
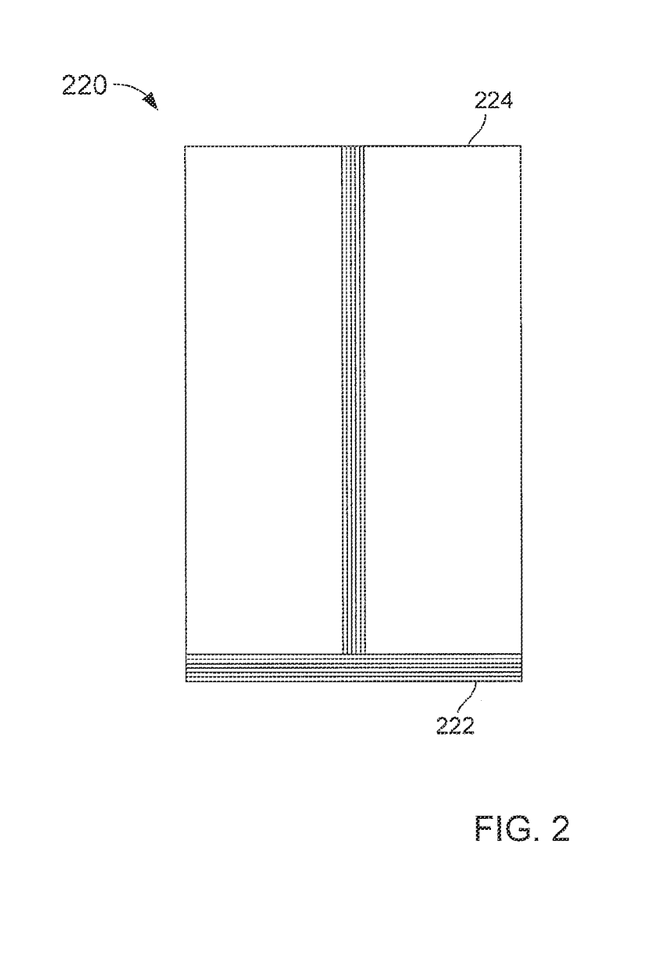
FIG. 2 is an illustration of a package according to an embodiment.

In some embodiments, system 100 can include a package sealing module (not shown), similar to sealing module 116 described herein, configured to seal the package after packing module 102 inserts the cloth into the package. For example, as shown in FIG. 2, the package 220 can include a first sealed end 222. The second end 224 may be left open for sealing at a later step in the process. Alternatively, as shown in FIG. 3, a package 320 can include a first sealed end 332 and a second sealed end 336.

Returning to FIG. 1, insertion module 104 can insert the package into a wrap (not shown), for example, a plastic sheet or film that surrounds the package, such as a polyethylene bag or other appropriate material. Said another way, the insertion module 104 can at least partially wrap the package in the film wrap. The wrap can at least partially enclose the package and can protect the package during transportation through system 100 and/or can ensure the sterile environment is maintained by the package after the package is sterilized. In some embodiments, insertion module 104 can insert a plurality of packages into a single wrap. In some embodiments, the wrap is sealed. In such embodiments, insertion module 104 can include a component configured to seal the wrap. In other such embodiments, system 100 can includes a wrap sealing module (not shown), similar to sealing module 116 described herein, configured to seal the wrap. In some embodiments, insertion module 104 can insert the package into two layers of wrap, or a wrap having a two-layer wall.

Sterilization module 106 can sterilize the package, and/or the package at least partially wrapped in wrap. In some embodiments, sterilization module 106 can irradiate the package. In such embodiments, sterilization module can expose the package to gamma radiation, for example, between about 25 kGy and about 50 kGy. In some embodiments, other sterilization methods can be used, for example, heat, ethylene oxide, and/or combinations of sterilization methods. As explained above, the present invention contemplates performing certain steps in a non-sterile environment. However, in order to preserve the sterility of the finished product, embodiments of the invention contemplate that the removal module 108, cutting module 112, filling module 114 and sealing module 116 will be located in one or more sterile environments.

Removal module 108 can remove the package from the wrap. In some embodiments, such as an embodiment where the wrap was sealed around the package, the removal module can be configured to cut and/or otherwise open the wrap. In some embodiments, system 100 can include a wrap cutting module (not shown) configured to cut and/or otherwise open the wrap.

In embodiments where the package includes a first sealed edge and a second sealed edge (see, e.g., FIG. 3), cutting module 112 can cut and/or otherwise open the package. In some embodiments, cutting module 112 can substantially remove the second sealed edge. In other embodiments, cutting module 112 can pierce the package and/or otherwise define an aperture in the package.

Filling module 114 can be configured to aseptically fill the package with a medical solution (not shown). Filling module 114 can include a filter (not shown) configured to filter the medical solution. The filter can be, for example, about a 0.2 μm/0.2 μm filter. In some embodiments, filling module 114 can include more than one filter. In such embodiments, the more than one filter can be arranged in series and/or parallel.

Filling module 114 can include a nozzle (not shown) configured to direct a flow of medical solution into the package. In some embodiments, filling module 114 can include and/or can be configured to be coupled to at least one storage location for storing medical solution before and/or after filtering.

In some embodiments, the medical solution can include chlorhexidine gluconate (hereinafter "CHG") solution and/or can include alcohol. In one such embodiment, the medical solution can include about 2%-4% CHG prior to filtering. In another such embodiment, the medical solution can include at least about 50% alcohol. In such embodiments, the medical solution can include about 70% alcohol. In another such embodiment, the medical solution can include about 2% CHG and at least about 50% alcohol. In some embodiments, other antimicrobial and/or antiseptic solutions can be used, for example, povidone iodine, para chloro meta xylenol, benzalkonium chloride, ethyl alcohol, etc. In some embodiments the medical solution can includes surfactants and/or other skin treatment/care compounds and/or solutions, preservatives, processing ingredients, inactive ingredients, etc.

Sealing module 116 can reseal the open end of the package, if the second sealed edge of the package was removed, and/or can seal the open end of the package, if the open end of the package was not previously sealed. Sealing module 116 can be configured to seal the package at a predetermined temperature and/or pressure, and the sealing module can be configured to seal the package such that an area within the package is at a predetermined pressure. In some embodiments, sealing module 116 can be an impulse heat sealer.

In some embodiments, the system 100 can include a stacking module (not shown) to stack, package and/or otherwise prepare the package for shipping and/or transportation to another room and/or destination.

Figure 4:
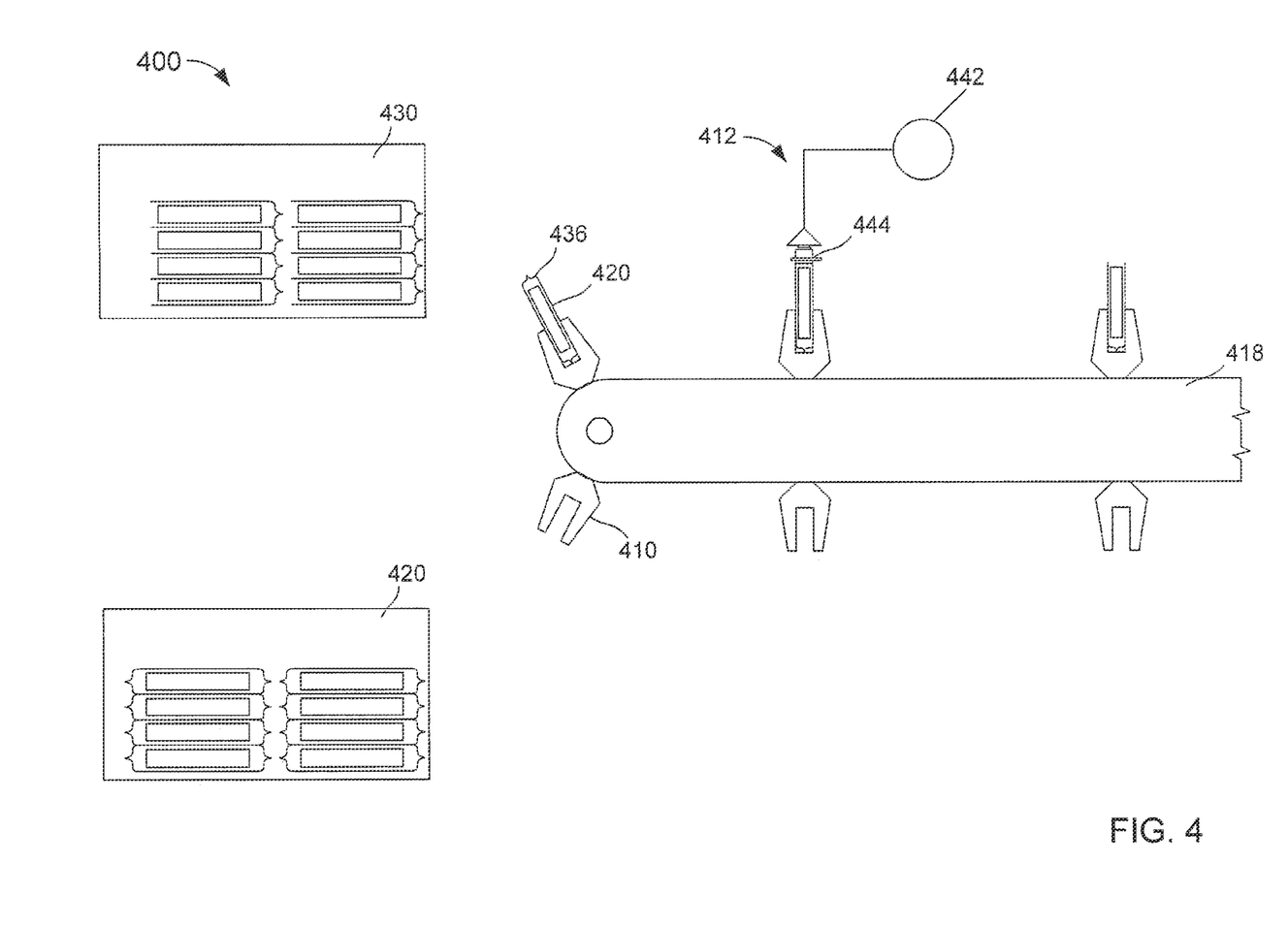
FIG. 4 is an illustration of a first portion of a room according to an embodiment.
Figure 5:
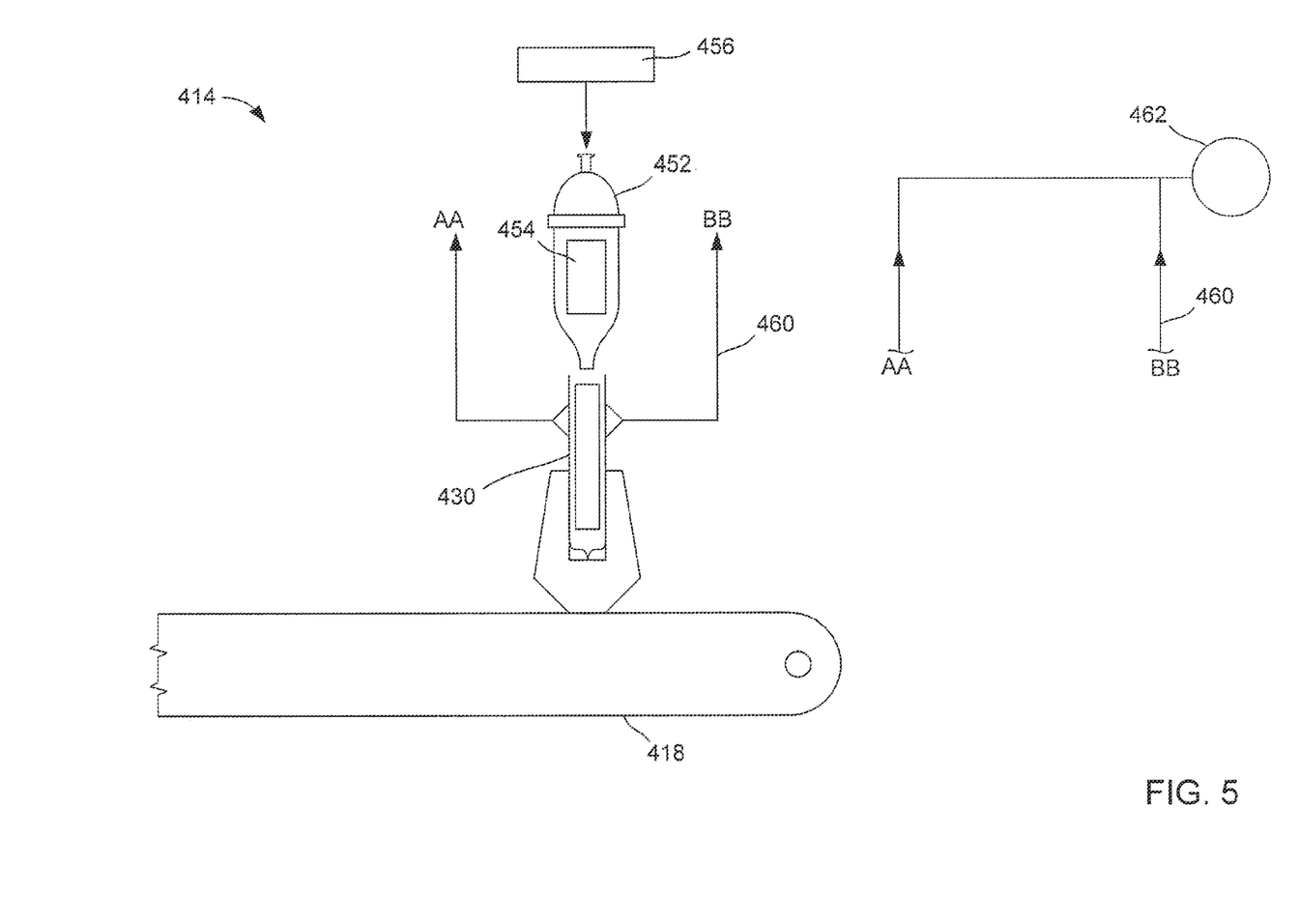
FIG. 5 is an illustration of a second portion of the room shown in FIG. 3.
Figure 6:
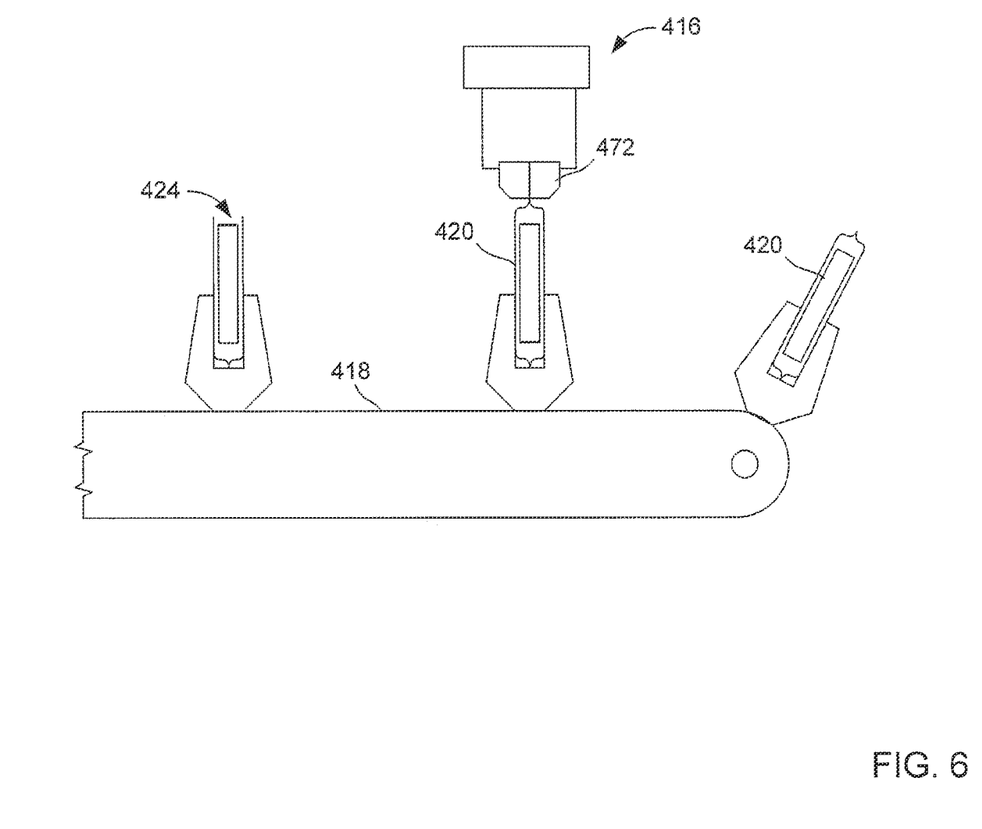
FIG. 6 is an illustration of a third portion of the room shown in FIG. 3.

FIGS. 4-6 depict portions of a room according to an embodiment that can include all or a portion of a system 400. System 400 can be similar to system 100 and can include similar components with similar characteristics. As shown in FIG. 4, system 400 can include a conveyor belt 418 configured to move packages 420 (including a sealed end) and/or packages 430 (including an open end) through system 400. System 400 can include a cutting module 412 that can include a vacuum system 442 configured to pull a closed end 436 of a package 420 into a knife assembly 444. Vacuum system 442 can include a vacuum pump 462 configured to exert a negative pressure on the package such that knife assembly 444 can cut, pierce or otherwise define an opening in package 420.

As shown in FIG. 5, system 400 can include a filling module 414. The filling module can include a dosing head and nozzle assembly 452 that includes at least one filter 454, and that is configured to direct a flow of a medical solution from a storage location 456 and into the package 420. Filling module 414 can include vacuum system 460 configured to hold open an open end and/or other opening of package 420 during the filling process. Vacuum system 460 can include a vacuum pump 462 configured to exert a negative pressure on the one or more portions of package 420. As shown in FIG. 6, system 400 can include a sealing module 416. Sealing module 416 can include a sealing bar 472 configured to seal an open end 424 of package 420.

By way of example, with reference to FIG. 4-6, two 8"×8" dry non-woven cloths, e.g. substantially free of medical solution and or other non-ambient moisture, can be disposed within a flexible package by a packaging module in a first room. The flex package can be sealed, and the package can include a first sealed edge and a second sealed edge. The flexible package can be inserted into a polyethylene bag (film). The polyethylene bag containing the package can be placed in a container approved for use in a clean room and configured to not impede sterilization. The container including the polyethylene bag and package can then be transported to a second room and sterilized via exposure to gamma radiation between about 25 kGy and about 50 kGy.

Continuing with the example, a medical solution can be prepared that includes 2%-4% CHG. The medical solution can be disposed in a storage location 456 and coupled to nozzle assembly 452 of filling module 414 which can be disposed in a third room that can be a clean room. The container can be transported to the third room and can be prepared for entrance into the third room in accordance with a predetermined clean room standard. Removal module can remove the package from the polyethylene bag, and package holder 410 and conveyor belt 418 can transport the package to cutting module 412. Vacuum system 442 of cutting module 412 can exert a negative pressure on the package and can pull the second sealed edge of the package into the knife assembly 444 of cutting module 412. Knife assembly 444 can remove the second edge 224 and/or otherwise define an opening in the package.

Continuing with the example, conveyor belt 418 can transport the package to filling module 414. The vacuum system 460 of filling module 414 can exert a negative pressure on at least one portion of the package such that the opening in the package is held open. Nozzle assembly 452 can dispense a predetermined amount of medical solution, for example, about 70 ml, from the storage location 456, through the filters 454 and into the package. Conveyor belt 418 can transport the package to the sealing module 416. The opening of the package can be positioned adjacent the sealing bar 472 of sealing module 416 and sealed. Conveyor belt 418 can then transport the package to a hopper or other module for further packaging.

While it is contemplated in some embodiments that the components of system 400 are located in a single sterile environment, the present invention also encompasses systems and methods in which the various steps described are located in separate rooms or environments. In such embodiments, the incomplete products may be moved from one environment to another in any appropriately sterile manner.

Figure 7:
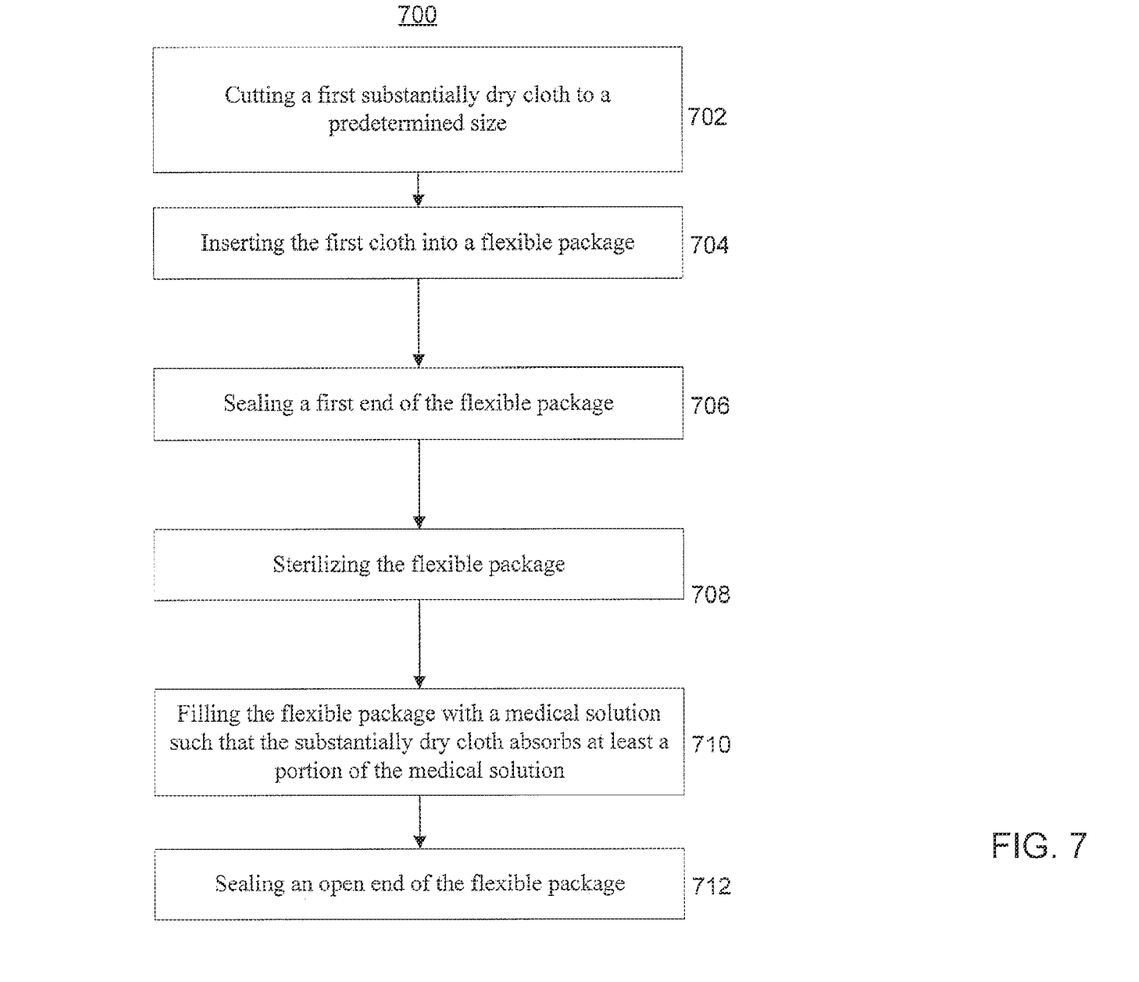
FIG. 7 is a flowchart showing a method of filling a package according to an embodiment.

FIG. 7 is a flowchart depicting a method 700 of aseptically filling a package. The method 700 can includes a first stage and a second stage. The first stage of method 700 can be performed in a non-sterile environment and can include cutting a first substantially dry cloth to a predetermined size, at 702. The first stage can include inserting the first cloth into a flexible package, at 704. The first stage can include sealing a first end of the flexible package, at 706. The first stage can include sterilizing the flexible package, at 708. The second stage of method 700 can be performed in a sterile environment and can include filling the flexible package with a medical solution such that the substantially dry cloth absorbs at least a portion of the medical solution, at 710. The second stage can include sealing an open end of the flexible package, at 712.

Figure 8:
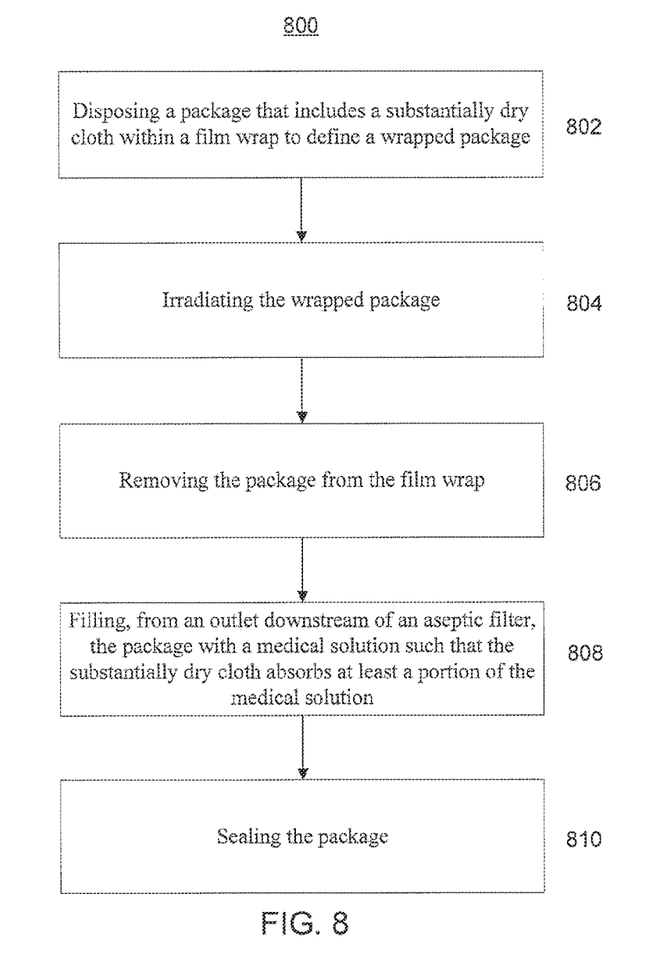
FIG. 8 is a flowchart showing a method of filling a package according to an embodiment.

FIG. 8 is a flowchart depicting a method 800 of aseptically filling a package. Method 800 includes disposing a package that includes a substantially dry cloth within a film wrap to define a wrapped package, at 802. Method 800 includes irradiating the wrapped package, at 804. Method 800 includes removing the package from the wrap, at 806. Method 800 includes filling, from an outlet downstream of an aseptic filter, the package with a medical solution such that the substantially dry cloth absorbs at least a portion of the medical solution, at 806. Method 800 includes sealing the package, at 810.

An embodiment of the present invention comprises the steps of: (1) package two 8 inch by 8 inch cloths dry (without solution or moisture) in flexible film container at using appropriate sealing temperatures and parameters for 0.48 mil PET/0.48 mil PET/2.25 mil HDPE COEX film; (2) after sealing, secure packages in two layers of polyethylene bags and place in clean room and radiation appropriate outer container; (3) sterilize packages using a range from 25-50 kGy; (4) prepare 2% CHG solution containing glucono-delta-lactone and fill into pre-sterilized container for transfer into aseptic environment; (5) prepare sterile filtering apparatus by appropriate cleaning including pump, tubing, stands, sealer, etc. for transfer into aseptic environment; (6) prepare post irradiated packages by appropriate cleaning for entry into Class 100 laminar flow environment for aseptic filling; (7) remove packages from inner polyethylene bag and transfer into the Class 100 area; (8) cut one end of the package with pre-sterilized surgical scissors; (9) using pre-programmed pump settings fill packages with 2% CHG Solution using 0.2 μm/0.2 μm sterile filter and peristaltic pump to a target fill volume of 70 ml; (10) reseal the open end using a sealer at pre-defined temperature and pressure settings; (11) remove sterile filled packages from Class 100 environment.

In an alternative embodiment, hard packages made of polyethylene or other appropriate material may be used. Such hard packages may comprise tubs using separate or flip-top lids. If such a hard package is used, the packages will be punctured, aseptically filled with solution, and sealed. Alternatively, the process could include shrink wrapping a tub without the lid, sterilizing the tubs and lids separately, removing the shrink wrap, aseptically filling the tubs, sealing and placing the lids on the tubs, and shrink wrapping the tubs and lids.

While various embodiments have been described above, it should be understood that they have been presented by way of example only, and not limitation. Where methods described above indicate certain events occurring in certain order, the ordering of certain events can be modified. Additionally, certain of the events can be performed concurrently in a parallel process when possible, as well as performed sequentially as described above. Although various embodiments have been described as having particular features and/or combinations of components, other embodiments are possible having a combination of any features and/or components from any of embodiments where appropriate. Furthermore, while certain temperatures, pressures, and other measurements, calculations, and/or other values are described in approximate terms, the values used are not meant to be exact and a range of values can be used, for example plus or minus 10 percent.

While the present disclosure and what the best modes of the inventions have been described in a manner establishing possession hereof by the inventors and enabling those of ordinary skill in the art to make and use the same, it will be understood and appreciated that there are many equivalents to the exemplary embodiments disclosed herein and that modifications and variations may be made thereto without departing from the scope and spirit of the inventions, which are to be limited not by the exemplary embodiments but by the appended claims.

What is claimed:

1. A method comprising:
   disposing a package that includes a substantially dry cloth within a wrap to form a wrapped package;
   irradiating the wrapped package;
   removing the package from the wrap;
   filling, from an outlet downstream of an aseptic filter, the package with a medical solution such that the substantially dry cloth absorbs at least a portion of the medical solution; and
   sealing the package.

2. The method of claim 1, wherein in the package is a flexible package.

3. The method of claim 1, wherein in the package is substantially rigid.

4. The method of claim 1, further comprising:
   prior to disposing the package within the wrap, sealing the package; and
   prior to filling the package, forming an opening in the package.

5. The method of claim 1, wherein irradiating the wrapped package comprises exposing the wrapped package to between about 25 kGy and about 50 kGy.

6. The method of claim 1, wherein the wrap comprises a double-walled wrap.

7. A method comprising:
   inserting a substantially dry cloth into a package;
   at least partially wrapping the package in a wrap to form a wrapped package;
   irradiating the wrapped package;
   removing the package from the wrap;
   filling the package with a medical solution such that the substantially dry cloth absorbs at least a portion of the medical solution; and
   sealing the package.

8. The method of claim 7 further comprising sealing the wrap.

9. The method of claim 7, wherein at least partially wrapping the package in a wrap comprises at least partially wrapping the package in a first layer of wrap and at least partially wrapping the package in a second layer of wrap.

10. The method of claim 7, wherein the wrap comprises multiple layers.

11. The method of claim 7 further comprising the step of passing the medical solution through an aseptic filter.

12. A method comprising:
    inserting a substantially dry cloth into a package;
    inserting the package in a wrap;
    sterilizing the wrap and the package;
    removing the package from the wrap;
    filling the package with a medical solution such that the substantially dry cloth absorbs at least a portion of the medical solution; and
    sealing the package.

13. The method of claim 12, wherein inserting the package in a wrap comprises inserting a single package in a single wrap.

14. The method of claim 12, wherein inserting the package in a wrap comprises inserting multiple packages in a single wrap.

15. The method of claim 12, wherein sterilizing the wrap and the package comprises irradiating the wrap and the package.

16. The method of claim 12 further comprising opening the package.

17. The method of claim 16 wherein opening the package comprises cutting the package.

18. The method of claim 16 further comprising sealing the package a second time.

19. The method of claim 12 further comprising sealing the wrap.

20. The method of claim 19 further comprising opening the wrap.

* * * * *